(12) United States Patent
Rietzel

(10) Patent No.: US 7,818,045 B2
(45) Date of Patent: Oct. 19, 2010

(54) METHOD FOR REDUCED-ARTIFACT RADIOLOGICAL 3D IMAGING, MEDICAL IMAGING DEVICE AND METHOD FOR CREATING A THERAPY PLAN

(75) Inventor: Eike Rietzel, Darmstadt (DE)

(73) Assignee: Siemens Aktiengesellschaft, Muchin (DE)

( * ) Notice: Subject to any disclaimer, the term of this patent is extended or adjusted under 35 U.S.C. 154(b) by 477 days.

(21) Appl. No.: 11/522,257

(22) Filed: Sep. 15, 2006

(65) Prior Publication Data

US 2007/0083101 A1    Apr. 12, 2007

Related U.S. Application Data

(60) Provisional application No. 60/717,831, filed on Sep. 16, 2005.

(30) Foreign Application Priority Data

Sep. 16, 2005   (DE) .................. 10 2005 044 407

(51) Int. Cl.
*A61B 5/05* (2006.01)
*G06K 9/00* (2006.01)
*G06T 15/00* (2006.01)

(52) U.S. Cl. .............. 600/425; 600/407; 600/424; 382/131; 345/419

(58) Field of Classification Search ............ None
See application file for complete search history.

(56) References Cited

U.S. PATENT DOCUMENTS

| 5,329,567 A | 7/1994 | Ikebe |
| 7,102,144 B2 * | 9/2006 | Matsuda et al. .......... 250/492.1 |
| 2001/0014140 A1 | 8/2001 | Proksa et al. |
| 2006/0020200 A1 * | 1/2006 | Medow et al. .............. 600/425 |
| 2007/0276215 A1 * | 11/2007 | Ziegler ....................... 600/407 |

FOREIGN PATENT DOCUMENTS

EP        0562 585 A2        9/1993

\* cited by examiner

*Primary Examiner*—Long V Le
*Assistant Examiner*—Angela M Hoffa

(57) ABSTRACT

A method for reduced-artifact 3D-imaging of an imaging volume having an interfering element. A patient is positioned in a first position and a second positions spatially different from each other in an imaging device and first 3D-imaging and second 3D-imaging are performed with the interfering element lying within a first radiographic layer and a second radiographic layer. A first and second set of raw data of the imaging volume are provided with the first set having artifact-influenced raw data for the first radiographic layer and the second set having artifact-influenced raw data for the second radiographic layer and non-artifact influenced raw data for the first radiographic layer. A reduced-artifact 3D data set is created by combining the raw data sets or by calculating a first 3D image data set and a second 3D image data set from the raw data sets and combining the 3D image data sets.

12 Claims, 2 Drawing Sheets

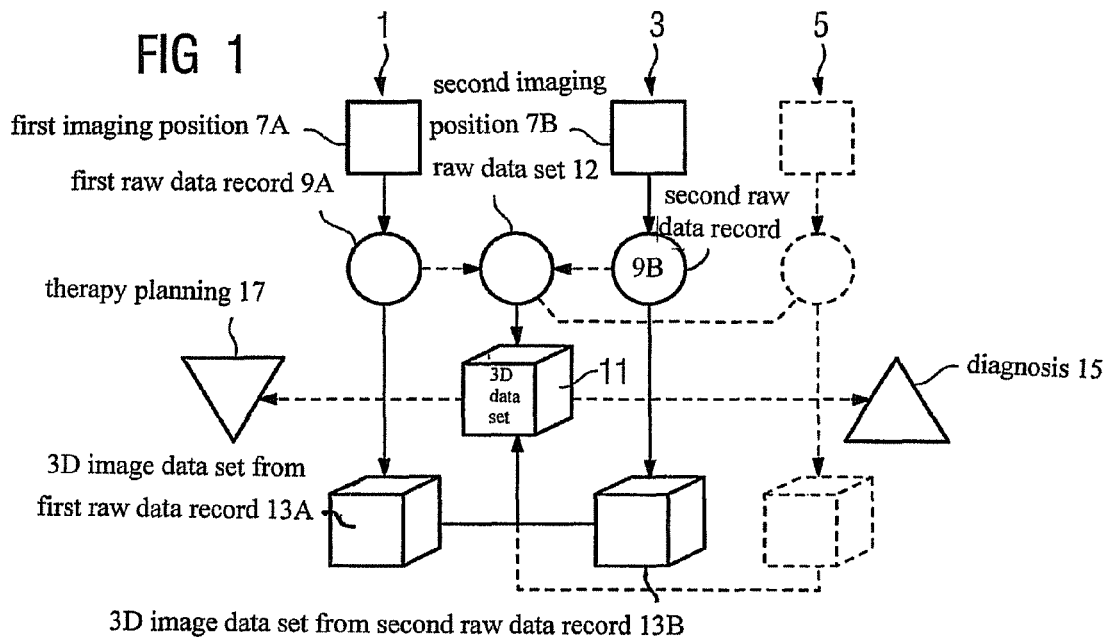
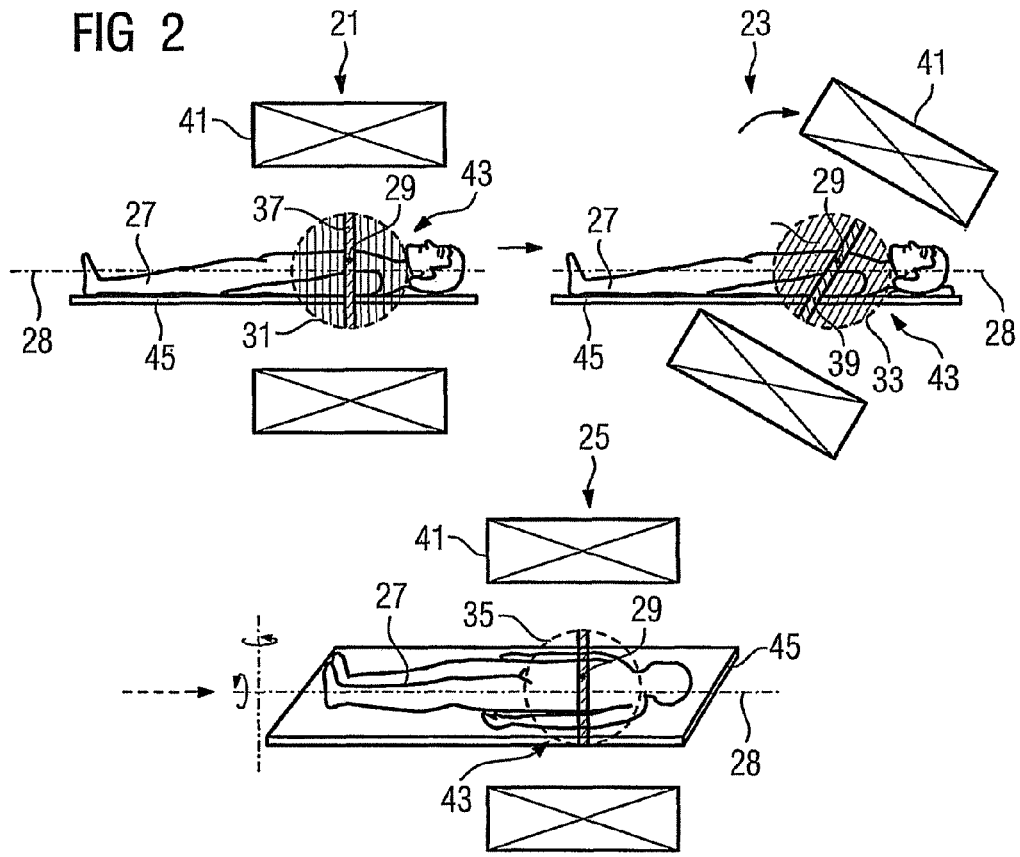

METHOD FOR REDUCED-ARTIFACT RADIOLOGICAL 3D IMAGING, MEDICAL IMAGING DEVICE AND METHOD FOR CREATING A THERAPY PLAN

CROSS REFERENCE TO RELATED APPLICATIONS

The present application claims the benefit of the provisional patent application filed on Sep. 16, 2005, and assigned application Ser. No. 60/717,831. The present application also claims priority of German application No. 10 2005 044 407.5 filed on Sep. 16, 2005. Both of the applications are incorporated by reference herein in their entirety.

FIELD OF THE INVENTION

The invention relates to a method for reduced-artifact radiological 3D imaging of an imaging volume of a medical imaging device, whereby the imaging volume features at least one interfering element causing an artifact. The invention further relates to a medical imaging device for creating a 3D radiological image data set as well as to a method for creating a therapy plan for irradiating a patient with particles of a particle therapy system.

BACKGROUND OF THE INVENTION

In radiological imaging with a computer tomography (CT) device for example, materials with high density, e.g. tooth fillings or artificial hips, lead to a complete absorption of the x-radiation on which the imaging is based. Such interfering elements in the area of a patient to be examined radiographically thus cause the loss of evaluable projection data. This means that the reconstruction of an image data set from such raw data for anatomical areas and which lie in the direction of radiological examination in front of and behind the interfering elements with high-density becomes imprecise and no longer meaningful. The effects resulting from an inadequately executable reconstruction in a 3D image data record are referred to as metal artifacts. The effects are not restricted to the region of the material with the high density but also affect other radiographic layers in which the interfering element lies.

A radiological imaging restricted in this way has a particular effect on the accuracy of therapy planning for a radiation therapy, especially for a particle therapy. In therapy planning dose and/or extent are calculated precisely on the basis of the density distribution measured during CT imaging. The decisive factor in the extent calculation and thereby for the accuracy of the dose distribution is the availability of a very precise density distribution of the tissue, measured in HU (Houndsfield Units) as a measure of the attenuation of x-ray radiation. This is because the local attenuation of the radiation in the patient is calculated by means of the HUs obtained from a radiology planning CT recording. An improved, i.e. reduced-artifact imaging thus has a positive effect on accuracy in therapy planning.

Usually layers and angular areas in which complete absorption of the radiation has occurred are determined for the imaging and therapy planning in the imaging data set before the reconstruction and are interpolated with surrounding projection data/raw data. In this case it is ensured that the projection data is completed as realistically as possible. Another procedure which is currently being applied in radiation therapy is to manually set the HU values in the CT imaging area which are affected by metal artifacts to a value which is to a certain degree sensible. Despite this, radiation directions of therapy radiation/therapy particle radiation in which not-insignificant metal artifacts have occurred are often excluded for radiological examination. Alternatively these types of interfering elements can for example be mechanically removed or, such as with the tooth fillings for example, be replaced by non-interfering materials such as plastic for example.

SUMMARY OF THE INVENTION

One object of the invention is to make it possible to obtain reduced-artifact image data where possible in radiological imaging. A further object is to provide an image data set to for therapy planning which allows an exact dose and/or extent calculation even in regions which are affected by interfering elements.

The object of the method in relation to reduced-artifact radiological 3D imaging is achieved by the method as claimed in the first independent claim. Furthermore the object is achieved by a medical imaging device as claimed in the second independent claim. The object in relation to the creation of a therapy plan is achieved by a method for creating a therapy plan as claimed in the third independent claim.

An advantage of the invention lies in the fact that the determination of HU values of the tissue of the patient is improved. I.e. the regions of an image data set affected by artifacts are reduced in their extent compared to conventional 3D image data sets. This has the effect in therapy planning of improving the extent calculation and thereby of increasing the precision in the irradiation. In diagnostics, because of the reduction of metal artifact-affected regions, anatomical areas which were not previously visible because of the artifacts can be assessed.

In one embodiment of the invention obtaining the data of an object to be scanned is undertaken with two or more imaging steps which have different tilt settings of a CT gantry. In the different imaging processes the artifact-affected regions are formed in different spatially arranged radiographic layers. In addition to a tilting, movement or turning of the CT gantry for example (in general of the imaging device) the object under investigation to be scanned can also be moved, turned or tilted relative to the CT device for example. The latter also causes a change to the artifact-affected regions in the imaging volume.

In a method of this type the area which can no longer be constructed because of for example the complete absorption of the x-ray radiation lies at different positions in the different reconstructions; i.e., different raw data or image data elements are affected by the interfering elements. With this data the areas which have been affected by the interfering elements are defined in all reconstructed imaging volumes. Their relative position in relation to each other is known uniquely through the setting in the imaging, e.g. relative tilt angle of the tilt settings. An image data set can be obtained through a combination of imaging volume elements from the different imaging recordings, said data set then featuring few or even no artifacts at all caused by the interfering elements.

In an alternative embodiment the reconstruction is already executed with a modified reconstruction algorithm which investigates the raw data of the different projections before the reconstruction of the image data set with regard to artifact-related errors and minimizes such image errors by correspondingly combining the projection data for the image to be calculated.

The imaging positions underlying the different imaging recordings can be effected by a shift, tilt or turning of the patient and/or of the imaging device. Where possible the imaging positions differ such that the effects of the artifacts are restricted to areas of the imaging volume which are as different as possible and only overlap slightly. This has the advantage that the influence of the interfering elements can be reduced in the ideal case to the interfering element itself.

In an embodiment of the method for generating a therapy plan for radiation therapy, especially for radiological examination a patient with particles of a particle therapy system, a radiological image which has its artifacts reduced as much as possible is generated with the aid of the imaging of spatially differently arranged imaging volumes. This reduced-artifact radiological image data set is then used as a basis for determining radiological parameters such as radiological examination area, dose distribution, particle beam energy and/or particle beam intensity.

Further advantageous embodiments with the invention are identified by the features of the subclaims.

BRIEF DESCRIPTION OF THE DRAWINGS

A number of exemplary embodiments of the invention are explained below with reference to FIGS. 1 to 5. The figures show:

FIG. 1 a typical illustration of an inventive imaging process and its application.

FIG. 2 different imaging positions of a patient to be scanned,

DETAILED DESCRIPTION OF THE INVENTION

Figure 3:
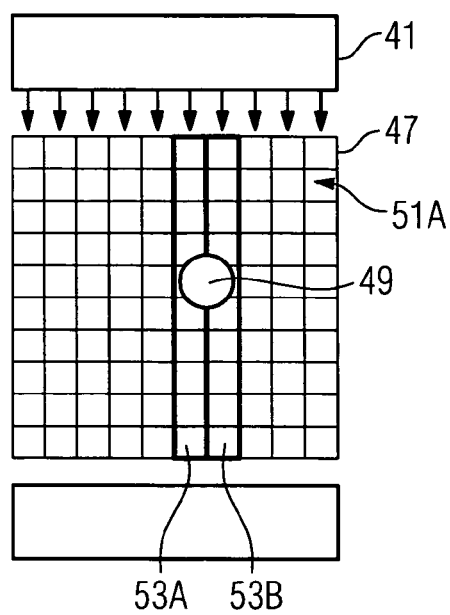
FIG. 3 and 4 corresponding effects of a metal element on the imaging.

FIG. 1 shows a typical schematic flow diagram to illustrate the procedure for generating reduced-artifact image data. The method is illustrated on the basis of two imaging procedures 1 and 3, in which case further imaging procedures 5 (as shown by dashed lines) can also be included. Each of the imaging procedures 1,3, 5 begins with a positioning process in which a patient is positioned in a first imaging position 7A or a second imaging position 7B within an imaging device (for an illustration see FIG. 2 with associated description). 3D-imaging is performed in each of the imaging positions 7A, 7B in which a set of radiographic layers are radiographically examined in each case with a radiographic source and are recorded positionally-resolved by a radiation detector. This creates a first raw data record 9A or a second raw data record 9B and this is prepared for further processing. The decisive point is now that the imaging positions 7A and 7B differ from each other in their geometrical arrangement to the radiology device, since only then does an interfering element in the first imaging process 1 lie in one (or in more) first radiographic layer(s) and in imaging process 3 in one (or in more) second radiographic layer(s). The radiographic layers intersect in a cross-sectional volume in which the interfering element also lies.

For further procedures for creating an image data set 11 which is as artifact-reduced as possible, a combination of the raw data sets 9A and 9B obtained can be used. In addition or as an alternative the calculation can be undertaken with the aid of 3D image data sets 13A and 13B, which have been calculated in each case from the raw data sets 9A or 9B. To this end for example image data elements which are affected by artifacts in the image data set 13B are replaced by their corresponding image data elements of the image data set 13A which are not influenced by artifacts.

The combination of the raw data sets 9A and 9B can for example produce a raw data set 12. The raw data set 12 and/or the two raw data sets 9A,9B can be used jointly in a correspondingly adapted reconstruction algorithm for obtaining the image data set 11.

The reduced-artifact 3D data set 11 on the one hand also allows a diagnosis 15 of the objects to be investigated in areas which would be adversely affected by artifacts in conventional imaging. Furthermore it is possible to use this data set for therapy planning 17 of a radiation therapy as a basis for calculating the ray or particle absorption in irradiation, in order for example to define necessary dosage distributions, beam intensities, particle energies or particle intensities for irradiation.

FIG. 2 typically shows three successive imaging processes 21, 23 and 25 each with different imaging positions, i.e. with different geometrical arrangements of the radiographic layers in relation to the patient 27. In the imaging process 21 the patient 27 is lying horizontally on his back, i.e., his longitudinal body axis 28 is e.g. at an angle of appr. 90° to the direction of illumination.

An interfering element 29—for example a heart pacemaker, a tooth crown, a metal implant etc.- can also be seen in the figure, as well as the sets 31, 33, 35 of radiographic layers aligned to the patient as a result of the imaging position and parallel to one another. The radiographic layer affected in each case by the interfering element 29 has been identified as a cross-hatched area for example the illumination layer 37 of the first imaging process 21 and the illumination layer 39 of the imaging process 23.

An imaging device 41 is for example a CT device, a cone-beam x-ray device or any other illumination device suitable for 3D imaging. It is preferably embodied so that it is able to be turned, tilted and moved, so that in an imaging volume 43 of the imaging device 41 the illuminated layers are aligned differently. The imaging process 23 is performed with the imaging device 41 tilted at an angle to the vertical, in which case the device has been tilted in the direction of the patient's longitudinal axis. The illuminated layers are correspondingly tilted at an angle to the horizontal.

The imaging device 41 features a patient support device, for example a patient table 45 or a patient chair. Preferably the device which holds the patient allows turning, tilting and/or movement of the patient 27, in order in its turn to enable different imaging positions to be selected. Thus for the imaging process 25 the patient 27 has been rotated both along an axis parallel to the longitudinal axis of the body 28 and also around a vertical axis.

FIG. 3 relates to an imaging process similar to the imaging process 21 shown in FIG. 2 and shows a section through a 3D image data set 47, in which an interfering element 49 and a an image element structure represented by small boxes 51 A can be seen with a number of perpendicular illumination layers. The interfering element 49 operates in the image data set on two adjacent illumination layers 53A and 53B.

Figure 4:
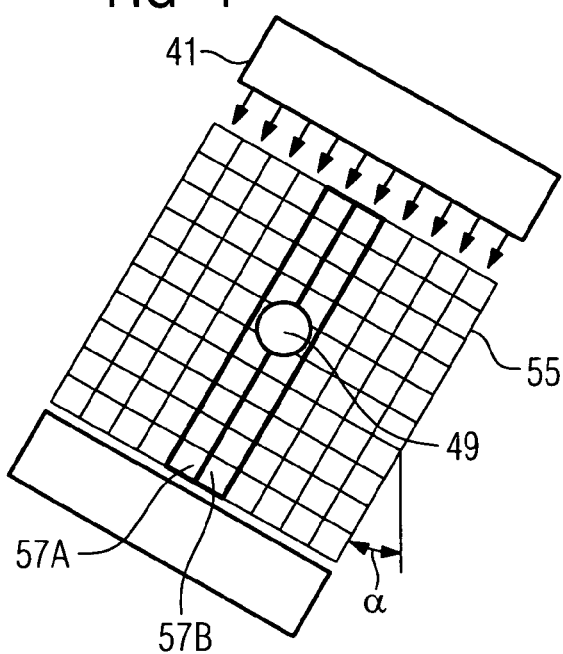

FIG. 4 shows a section through an image data set 55, which for example results from an imaging process corresponding to imaging process 23 from FIG. 2. The orientation of the illumination layers is rotated by an angle $\alpha$ to the vertically aligned illumination layers in FIG. 3. The interfering element 49 now operates on the illumination layers 57A and 57B.

Figure 5:
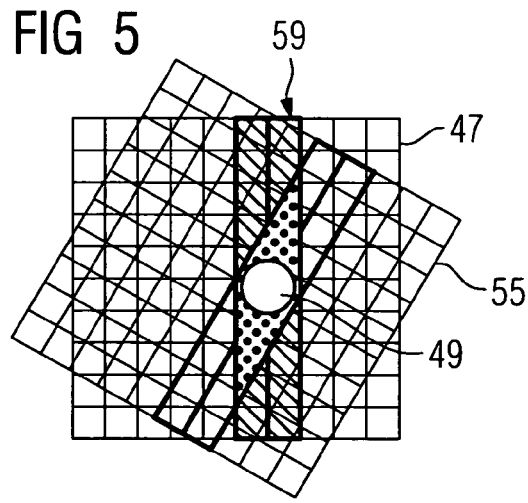
FIG. 5 obtaining a reduced-artifact image data set by means of the imaging used in FIG. 3 and 4.

FIG. 5 shows an overlaying of the image data sets 47 and 55. It can be seen that the image elements of the layers 53A, 53B or 57A, 57B influenced by the interfering element 49 only overlap in a restricted area. If for example the image data set 47 is taken as the basis, the image elements in the cross-hatched area 59 can be approximately replaced by the corresponding image elements of the image data set 55.

In order to fill the remaining dotted areas with measured HU values, an imaging process corresponding for example to imaging process 25 from FIG. 2 is needed, which is based on rotating the patient bed around the longitudinal axis of the patient as well as a rotation around the vertical axis. A 3D image data set corrected in this way satisfies the high demands imposed in radiotherapy for example.

The invention claimed is:

1. A method for generating an artifact-reduced 3D-image data set of an imaging volume having an interfering element, wherein the 3D-image data set is generated by a medical imaging device that collects image data from projections through an imaged object, comprising:

positioning a patient in a first imaging position in an imaging device;

generating a first 3D-imaging of the patient in the first imaging position with the interfering element lying within a first illumination layer;

defining an area within the imaging volume that is affected by the interfering element;

calculating a first raw data set of the imaging volume based on the first 3D-imaging comprising an artifact-influenced raw data for the first illumination layer, wherein the artifacts of the first raw data set are due to the interfering element;

positioning the patient in a second imaging position spatially different from the first imaging position;

generating a second 3D-imaging of the patient in the second imaging position with the interfering element lying within a second illumination layer intersecting with the first illumination layer in an intersection volume where the interfering element lies;

calculating a second raw data set of the imaging volume based on the second 3D-imaging comprising an artifact-influenced raw data for the second illumination layer, wherein the artifacts of the second raw data set are due to the interfering element;

calculating a first 3D image data set from the first raw data set;

calculating a second 3D image data set from the second raw data set;

calculating a non-artifact influenced data for the first 3D image data set outside the intersection volume based on the first 3D-imaging data uninfluenced by the interfering element or a non-artifact influenced data for the second 3D image data set outside the intersection volume based on the second 3D-imaging uninfluenced by the interfering element;

combining the first 3D image data set and the second 3D image data set to form a combined data set, wherein the non-artifact influenced data of one of the first or second 3D image data set is combined with the artifact influenced data of the other 3D image data set outside the intersection volume wherein a portion of the artifact-influenced data of the first or second 3D image data set is replaced by respective overlapping spatial locations of the non-artifact influenced data from the other 3D image data set; and calculating the artifact-reduced 3D-image data set of the imaging volume based on the combined data set.

2. The method as claimed in claim 1, wherein the second imaging position is positioned by moving, tilting or turning the patient.

3. The method as claimed in claim 1, wherein the second imaging position is positioned by moving, tilting or turning the imaging device.

4. The method as claimed in claim 1, wherein a further 3D-imaging with the interfering element lying within a further illumination layer is generated in a further different imaging position to provide a further raw data set which is combined with the first and second raw data sets.

5. The method as claimed in claim 1, wherein the interfering element is selected from the group consisting of: a heart pacemaker, a tooth crown, and a metal implant of the patient.

6. A medical imaging device system for generating an artifact-reduced 3D-image data set, wherein the medical imaging device collects image data from projections through an imaged object, comprising:

a patient supporting device;

an image device which:

records a first 3D-imaging of the patient in a first imaging position with an interfering element lying within a first illumination layer, records a second 3D-imaging of the patient in a second imaging position with the interfering element lying within a second illumination layer intersecting with the first illumination layer in an intersection volume in which the interfering element lies; and an image processing unit configured and arranged to:

define an area within the imaging volume that is affected by the interfering element;

calculate a first raw data set of the imaging volume based on the first 3D-imaging comprising an artifact-influenced raw data for the first illumination layer, wherein the artifacts of the first raw data set are due to the interfering element, calculate a second raw data set of the imaging volume based on the second 3D-imaging comprising an artifact-influenced raw data for the second illumination layer, wherein the artifacts of the second raw data set are due to the interfering element, calculate a first 3D image data set from the first raw data set, calculate a second 3D image data set from the second raw data set, calculate a non-artifact influenced data for the first 3D image data set outside the intersection volume based on the first 3D-imaging data uninfluenced by the interfering element or a non-artifact influenced data for the second 3D image data set outside the intersection volume based on the second 3D-imaging data uninfluenced by the interfering element, combine the first 3D image data set and the second 3D image data set to form a combined data set, wherein the non-artifact influenced data of the first or second 3D image data set is combined with the artifact influenced data of the other 3D image data set outside the intersection volume, wherein a portion of the artifact-influenced data of the first or second 3D image data set is replaced by respective overlapping spatial locations of the non-artifact influenced data from the other 3D image data set, and calculate the artifact-reduced 3D-image data set based on the combined data set.

7. The medical imaging device system as claimed in claim 6, wherein the imaging device is a computer tomography device comprising a gantry which is tiltable, turnable or movable.

8. The medical imaging device system as claimed in claim 6, wherein the patient supporting device is tiltable, turnable or movable.

9. The medical imaging device system as claimed in claim 6, wherein the second imaging position is spatially different from the first imaging position relative to the image device.

10. A method for creating a therapy plan for a radiotherapy for a patient, comprising:
   creating a reduced-artifact radiological image data set by an image device that collects image data from projections through an imaged object, comprising:
       positioning the patient in a first imaging position in the imaging device,
       defining an area within the imaging volume that is affected by the interfering element,
       generating a first 3D-imaging of the patient in the first imaging position with an interfering element lying within a first illumination layer,
       calculating a first raw data set based on the first 3D-imaging comprising an artifact-influenced raw data for the first illumination layer, wherein the artifacts of the first raw data set are due to the interfering element,
       positioning the patient in a second imaging position spatially different from the first imaging position,
       generating a second 3D-imaging of the patient in the second imaging position with the interfering element lying within a second illumination layer intersecting with the first illumination layer in an intersection volume in which the interfering element lies,
       calculating a second raw data set based on the second 3D-imaging comprising an artifact-influenced raw data for the second illumination layer, wherein the artifacts of the first raw data set are due to the interfering element,
       calculating a first 3D image data set from the first raw data set;
       calculating a second 3D image data set from the second raw data set;
       calculating a non-artifact influenced data for the first 3D image data set outside the intersection volume based on the first 3D-imaging data uninfluenced by the interfering element or a non-artifact influenced data for the second 3D image data set outside the intersection volume based on the second 3D-imaging data uninfluenced by the interfering element,
       combining the first 3D image data set and the second 3D image data set to form a combined data set, wherein the non-artifact influenced data of the first or second 3D image data set is combined with the artifact influenced data of the other 3D image data set outside the intersection volume wherein a portion of the artifact-influenced data of the first or second 3D image data set is replaced by respective overlapping spatial locations of the non-artifact influenced data from the other 3D image data set, and
   calculating the artifact-reduced radiological image data set based on the combined data set;
   selecting a radiological examination parameter based on the artifact-reduced radiological image data set; and
   planning the radiotherapy for the patient according to the radiological examination parameter.

11. The method as claimed in claim 10, wherein the radiotherapy is a radiological examination of the patient comprising a particle therapy system.

12. The method as claimed in claim 10, wherein the radiological examination parameter is selected from the group consisting of: examination area, dose distribution, particle beam energy and particle beam intensity.

* * * * *